United States Patent
Bell et al.

[11] Patent Number: 6,031,115
[45] Date of Patent: Feb. 29, 2000

[54] PROCESS FOR PREPARING EPOXIDES

[75] Inventors: David Bell; Michael Fedouloff; Gillian Turner, all of Harlow, United Kingdom

[73] Assignee: SmithKline Beecham plc, Middlesex, United Kingdom

[21] Appl. No.: 09/109,856

[22] Filed: Jul. 2, 1998

Related U.S. Application Data

[63] Continuation of application No. 08/893,610, Jul. 11, 1997, abandoned, which is a continuation of application No. 08/576,022, Dec. 21, 1995, abandoned, which is a continuation of application No. 08/411,034, Mar. 27, 1995, abandoned, which is a continuation of application No. 08/050,471, May 14, 1993, abandoned.

[51] Int. Cl.$^7$ ..................... C07D 319/14; C07D 491/00
[52] U.S. Cl. ....................... 549/362; 549/359; 549/518; 546/89; 546/115
[58] Field of Search ................... 549/359, 362, 549/518; 546/89, 115

[56] References Cited

FOREIGN PATENT DOCUMENTS

| | | |
|---|---|---|
| 296975 | 6/1988 | European Pat. Off. . |
| 376 524 | 12/1989 | European Pat. Off. . |
| WO 91/14694 | 10/1991 | WIPO . |

OTHER PUBLICATIONS

N. Lee et al, Tetrahedron Letters; vol. 32, No. 38 pp. 5055–5068, 1991.

*Primary Examiner*—Amelia Owens
*Attorney, Agent, or Firm*—Mary E. McCarthy; Stephen Venetianer; Charles M. Kinzig

[57] ABSTRACT

A process for preparing compounds of formula (B)

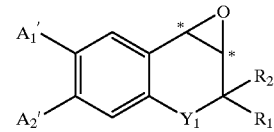

(B)

wherein:
one of $A_1'$ or $A_2'$ represents hydrogen and the other represents a group $CF_3$—Y— wherein Y represents —$CF_2$—, >C=O, or —CH(OH)—, or $A_1'$ and $A_2'$ are groups convertible to $A_1$ and $A_2$ respectively.

$Y_1$ represents —O—, —$CH_2$— or $NR^O$ wherein $R^O$ is hydrogen, alkyl or alkylcarbonyl; $R_1$ and $R_2$ independently represent hydrogen or alkyl; or $R_1$ and $R_2$ together represent a $C_{2-7}$ polymethylene moiety;

$R_3$ represents hydrogen, hydroxy, alkoxy or acyloxy and $R_4$ is hydrogen or $R_3$ and $R_4$ together represent a bond;

which process comprises reacting a compound of formula (C):

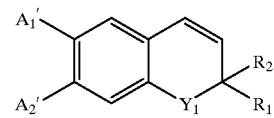

(C)

wherein the variable $A_1'$, $A_2'$, $Y_1$, $R_1$ and $R_2$ are as defined above, in the presence of an oxygen source and a chiral catalyst as defined in WO/91/14694.

9 Claims, No Drawings

PROCESS FOR PREPARING EPOXIDES

This application is a con of Ser. No. 08/893,610 filed Jul. 11, 1997, now abandoned, which is a continuation of Ser. No. 08/576,022, filed Dec. 21, 1995, now abandoned, which is a con Ser. No. 08/411,034 Mar. 27, 1995, now abandoned, which is a con of Ser. No. 08/050,471, May 14, 1993, now abandoned.

This invention relates to a novel process for preparing certain epoxides.

EP-A-0 376 524 describes certain compounds of formula (A):

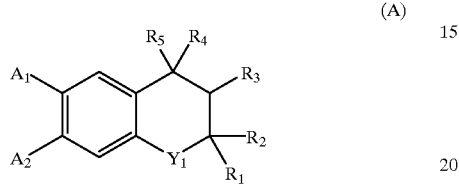

or, where appropriate, a pharmaceutically acceptable salt thereof, or a pharmaceutically acceptable solvate thereof wherein:

one of $A_1$ or $A_2$ represents hydrogen and the other represents a group $CF_3$—Y— wherein Y represents —$CF_2$—, >C═O, or —CH(OH)—;

Y represents —O—, —$CH_2$— or $NR^O$ wherein $R^O$ is hydrogen, alkyl or alkylcarbonyl; $R_1$ and $R_2$ independently represent hydrogen or alkyl; or $R_1$ and $R_2$ together represent a $C_{2-7}$ polymethylene moiety;

$R_3$ represents hydrogen, hydroxy, alkoxy or acyloxy and $R_4$ is hydrogen or $R_3$ and $R_4$ together represent a bond;

$R_5$ represents either a moiety of formula (a):

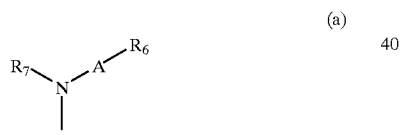

wherein A represents >C═X wherein X is O, S or $NR_8$ wherein $R_8$ represents CN, $NO_2$, $COR_9$ wherein $R_9$ is alkyl, amino, monoalkylamino, fluoroalkyl, phenyl or substituted phenyl or $R_8$ is $SO_2R_9$ wherein $R_9$ is as defined above, or A represents a bond;

when A represents >C═X wherein X is O or S, then $R_6$ is hydrogen; alkyl optionally substituted by one or more groups or atoms selected from halogen, hydroxy, alkoxyalkoxycarbonyl, carboxy or an ester or amide thereof, amino, monoalkylamino or dialkylamino; alkenyl; amino optionally substituted by an alkyl or alkenyl group or by an alkanoyl group optionally substituted by up to three halo atoms, by a phenyl group optionally substituted by alkyl, alkoxy or halogen; substituted or unsubstituted aryl or substituted or unsubstituted heteroaryl; and $R_7$ represents hydrogen or alkyl;

or $R_6$ and $R_7$ together represent a linking chain of formula —$A_3$—$A_4$—, $A_3$ being attached to the nitrogen atom of the moiety —N—A— and $A_4$ being attached to the group A on the said moiety, and wherein $A_3$ represents a substituted or unsubstituted methylene group, $A_4$ represents 2 or 3 linking members, one of the linking members optionally representing O, S or NR and the other linking members each independently representing a substituted or unsubstituted methylene group;

R represents hydrogen, alkyl, alkanoyl, phenyl $C_{1-4}$-alkyl, arylcarbonyl wherein the aryl group may be substituted or unsubstituted; or R is mono- or bi-cyclic- heteroarylcarbonyl;

when A represents >C═X wherein X represents $NR_8$, then $R_6$ represents —$NH.R_{10}$ wherein $R_{10}$ is hydrogen, alkyl, $C_{3-6}$ cycloalkyl, alkenyl or alkynyl and $R_7$ is hydrogen or alkyl; or $R_7$ and $R_{10}$ together represent $C_{2-4}$ polymethylene;

when A represents a bond, then $R_6$ and $R_7$ together with the nitrogen atom to which they are attached, form an unsaturated heterocyclic ring having 5 to 7 ring atoms, which ring atoms comprise up to 2 further nitrogen atoms and a carbon atom, the carbon atom being substituted with either an oxo group or a thioxo group, the remaining ring atoms being substituted or unsubstituted;

or $R_5$ represents a moiety of formula (b):

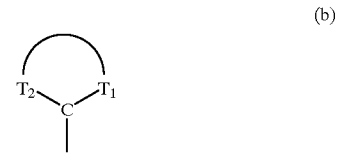

wherein $T_1$ represents >C—OH or $N(O)_n$ wherein n is zero or 1 and $T_2$ together with C—$T_1$, when $T_1$ is >C—OH, represents an optionally substituted aryl group or $T_2$ together with $CT_1$, when $T_1$ is $N(O)_n$, represents an optionally substituted, N— heteroaryl group;

or $R_5$ represents a moiety of formula (c):

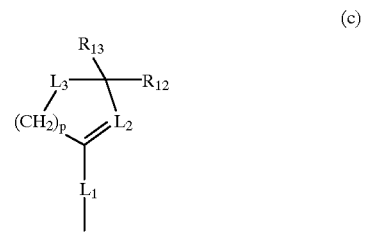

wherein $L_1$ represents O or $NR_{11}$ wherein $R_{11}$ represents hydrogen, alkyl, formyl, acetyl or hydroxymethyl, $L_2$ represents N or $CL_4$ wherein $L_4$ is hydrogen, halogen, formyl or hydroxymethyl, $L_3$ represents $CH_2$, O, S, >$CHL_5$ wherein $L_5$ is halogen or $NL_6$ wherein $L_6$ is hydrogen or alkyl and $R_{12}$ and $R_{13}$ each independently represent hydrogen or alkyl or $R_{12}$ together with $R_{13}$ represents oxo or thioxo; and p represents 1,2 or 3; which compounds are described as being useful as smooth muscle relaxants.

A useful intermediate in the preparation of compounds of formula (A) is an epoxide of formula (B):

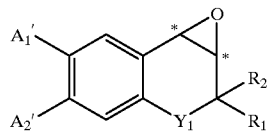

(B)

wherein $A_1'$ and $A_2'$ are $A_1$ or $A_2$ as defined in relation to formula (A), or groups convertible thereto and $R_1$, $R_2$ and $Y_1$ are as defined in relation to formula (A).

The carbon atoms marked with an asterisk (*) on formula (B) are chiral carbon atoms.

Previously, chemical methods for preparing the epoxide of formula (B) resulted in the formation of a racemic mixture of the epoxide: Any compound of formula (A) produced from such an epoxide would also be racemic and hence would need to be resolved to yield an optically pure product.

WO 91/14694 describes certain catalysts which may be used for enantioselectively epoxidizing prochiral olefins. However, there is no mention that such catalysts could be used to prepare substantially enantiomerically pure chiral epoxides of formula (B).

Surprisingly a new process has now been found which uses particular catalysts from WO 91/14694 to produce the chiral epoxide of formula (B) in substantially enantiomerically pure form thus obviating the need for any resolution when preparing compounds of formula (A).

Accordingly, the present invention provides a process for preparing compounds of formula (B) (hereinbefore described) which process comprises reacting a compound of formula (C):

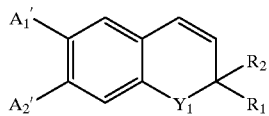

(C)

wherein $A_1'$, $A_2'$, $R_1$, $R_2$ and $Y_1$ are as defined in relation to formula (B) in the presence of an oxygen source and a chiral catalyst wherein the chiral catalyst is selected from the group consisting of compounds with the structure of formula (D):

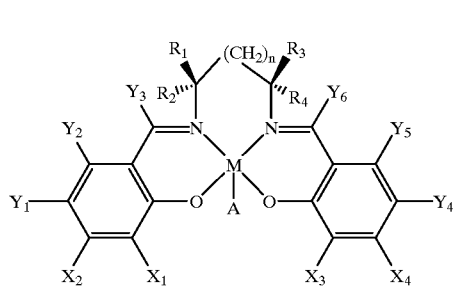

(D)

wherein M is a transition metal ion, A is an anion, and n is either 0, 1, or 2; at least one of X1 or X2 is selected from the group consisting of silyl, aryl, secondary alkyl and tertiary alkyl; and at least one of X3 or X4 is selected from the same group; Y1, Y2, Y3, Y4, Y5, and Y6 are independently selected from the group consisting of hydrogen, halide, alkyl, aryl group, silyl group, and alkyl group bearing hetero-atoms such as alkoxy and halide; and at least one of R1, R2, R3 and R4 is selected from a first group consisting of H, $CH_3$, $C_2H_5$, and primary alkyl; wherein if R1 is selected from said first group, then R2 and R3 are selected from a second group consisting of aryl groups, heteroatom-bearing aromatic groups, secondary alkyls and tertiary alkyls; if R2 is selected from said first group, then R1 and R4 are selected from said second group; if R3 is selected from said first group, then R1 and R4 are selected from said second group; if R4 is selected from said first group, then R2 and R3 are selected from said second group; or compounds with the structure of formula (I):

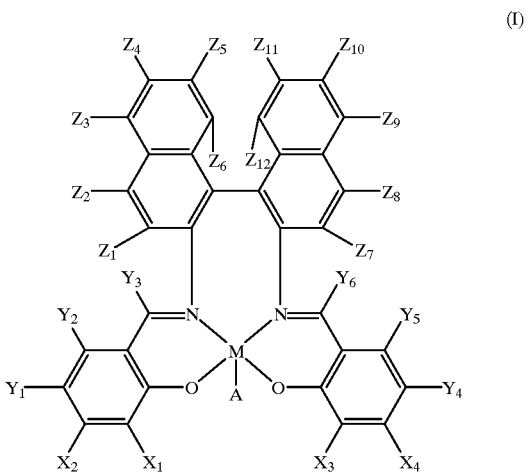

(I)

wherein M is a transition metal ion and A is an anion; where at least one of X1 or X2 is selected from the group consisting of aryl, primary alkyl, secondary alkyl, tertiary alkyl, and hetero atoms; where at least one of X3 or X4 is selected from the group consisting of aryl, primary alkyl, secondary alkyl, tertiary alkyl, and hetero atoms; and where Y1, Y2, Y3, Y4, Y5, Y6, Z1, Z2, Z3, Z4, Z5, Z6, Z7, Z8, Z9, Z10, Z11, and Z12 are independently selected from the group consisting of hydrogen, halide, alkyl, aryl, and alkyl group bearing hetero atoms; or compounds with the structure of formula (J):

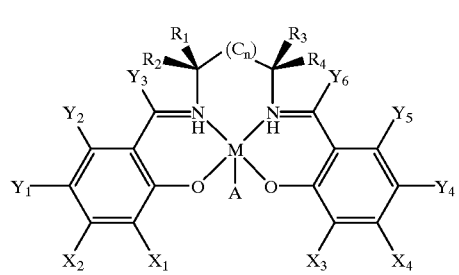

(J)

where M is a transition metal ion and A is an anion; where n is either 0, 1, or 2; where at least one of X1 or X2 is selected from the group consisting of aryl, primary ally, secondary alkyls tertiary alkyl, and hetero atoms; where at least one of X3 or X4 is selected from the group consisting of aryl, primary alkyl, secondary alkyl, tertiary alkyl, and hetero atoms; where at least one of Y1 or Y2 is selected from the group consisting of aryl, primary alkyl, secondary alkyl, tertiary alkyl, and hetero atoms; where at least one of Y4 or Y5 is selected from the group consisting of aryl, primary alkyl, secondary alkyl, tertiary alkyl, and hetero atoms; where Y3 and Y6 are independently selected from the group consisting of hydrogen and primary alkyl groups; where either one or two of R1, R2, R3 and R4 is hydrogen; where, if R1 is hydrogen, then R3 is a primary alkyl; where, if R2 is hydrogen, then R4 is a primary alkyl; where, if R3 is hydrogen, then R1 is a primary alkyl; and where, if R4 is hydrogen, then R2 is a primary alkyl; or compounds with the structure of formula (K):

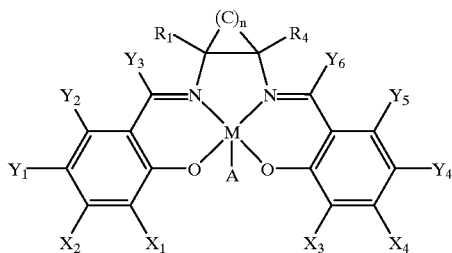

(K)

where M is a transition metal ion and A is an anion; where n is either 3, 4, 5 or 6; where at least one of X1 or X2 is selected from the group consisting of aryl, primary alkyl, secondary alkyls tertiary alkyl, and hetero atoms; where at least one of X3 or X4 is selected from the group consisting of aryl, primary alkyl, secondary alkyl, tertiary alkyl, and hetero atoms; where at least one of Y1 or Y2 is selected from the group consisting of aryl, primary alkyl, secondary alkyl, tertiary alkyls, and hetero atoms; where at least one of Y4 or Y5 is selected from the group consisting of aryl, primary alkyl, secondary alkyl, tertiary alkyl, and hetero atoms; where Y3, and Y6 are independently selected from the group consisting of hydrogen and primary alkyl groups; where R1 and R4 are trans to each other and at least one of R1 and R4 is selected from the group consisting of primary alkyl and hydrogen; and where the carbons in the $(C)_n$ portion have substituents selected from the group consisting of hydrogen, alkyl, aryl, and heteroatoms.

The chiral catalyst is especially those of formula (D):

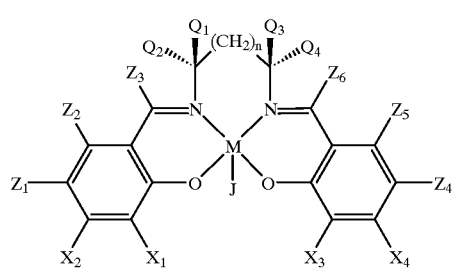

(D)

in which
M is a transition metal ion, J is an anion, and n is either 0, 1 or 2; at least one of $X_1$ or $X_2$ is selected from the group consisting of silyls, aryls, secondary alkyls and tertiary alkyls; and at least one of $X_3$ or $X_4$ is selected from the same group, $Z_1$, $Z_2$, $Z_3$, $Z_4$, $Z_5$ and $Z_6$ are independently selected from the group consisting of hydrogen, halides, alkyls, aryl groups, silyl groups, and alkyl groups bearing heteroatoms such as alkoxy and halide, also, at least one of $Q_1$, $Q_2$, $Q_3$ and $Q_4$ is selected from a first group consisting of H, $CH_3$, $C_2H_5$ and primary alkyls, furthermore, if $Q_1$ is selected from said first group, then $Q_2$ and $Q_3$ are selected from a second group consisting of aryl groups, heteroatom-bearing aromatic groups, secondary alkyls and tertiary alkyls; if $Q_2$ is selected from said first group, then $Q_1$ and $Q_4$ are selected from said second group; if $Q_3$ is selected from said first group, then $Q_1$ and $Q_4$ are selected from said second group; if $Q_4$ is selected from said first group, then $Q_2$ and $Q_3$ are selected from said second group, and thereafter when $A_1'$ and/or $A_2'$ are groups convertible to $A_1$ and $A_2$ respectively; converting $A_1'$ and $A_2'$ to $A_1$ and $A_2$ respectively.

It should be appreciated that the bond between M and J has varying degrees of ionic character depending on the anion used.

Preferred values for $A_1'$, $A_2'$, $Y_1$, $R_1$ and $R_2$ in compounds of formula (C) are as defined in EP-A-0376 524.

Most preferably $A_1'$ is $CF_3CF_2$, $A_2'$ is hydrogen, $Y_1$ is oxygen and $R_1$ and $R_2$ are both methyl.

Preferred values for M, J, n, $X_1$, $X_2$, $X_3$, $X_4$, $Z_1$, $Z_2$, $Z_3$, $Z_4$, $Z_5$, $Z_6$, $Q_1$, $Q_2$, $Q_3$ and $Q_4$ are as defined in WO/91/14694.

A preferred sub-group of catalysts of formula (D) are of formula (E):

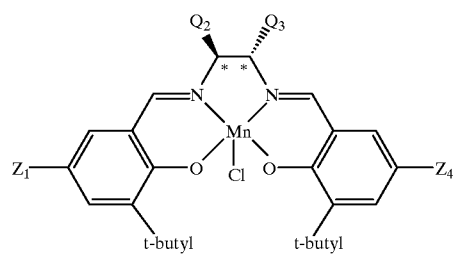

(E)

in which $Z_1$ and $Z_4$ are the same and are selected from the group consisting of methyl, t-butyl or methoxy and $Q_2$ and $Q_3$ are either both phenyl or together with the carbon atoms to which they are attached form an hexyl ring.

Most preferably, in catalysts of formula (E), $Z_1$ and $Z_4$ are both t-butyl and $Q_2$ and $Q_3$ together with the carbon atoms to which they are attached form an hexyl ring.

The reaction between the compound of formula (C) in the presence of an oxygen source and the chiral catalyst is suitably carried out using the procedures outlined in WO/91/14694 or procedures analogous thereto.

Suitably, the reaction is carried out as a two phase reaction with the compound of formula (C) and the chiral catalyst being disolved in an inert solvent such as dichloromethane and the other phase being water with sodium hypochlorite added as the oxygen source, optionally in the presence of a buffer such as sodium dihydrogen phosphate, the pH being suitably adjusted to a pH of between 10 and 13, preferably between 10.5 and 12, most preferably between 11 and 11.5

The reaction is suitably carried out at reduced, ambient or elevated temperature, preferably at elevated temperature, such as greater than 30° C., preferably greater than 35° C., most preferably at 40° C. to 45° C.

Suitably the mole ratio of chiral catalyst to compound of formula (C) is in the range of 0.01 to 10, preferably in the range of 1 to 5, most preferably in the range of 1 to 3.

Examples of groups $A_1'$ and $A_2'$ convertible to $A_1$ and $A_2$ are described herein. The conversion of $A_1'$ and $A_2'$ into $A_1$ and $A_2$ respectively may be carried out by conventional techniques. For example, $CF_3CO$— may be converted into $CF_3CH(OH)$— by reduction using potassiumborohydride in methanol at 0° C. $CF_3CO$— may be converted into $CF_3CF_2$— by using a convenient fluorinating agent, for example by using diethylaminosulphur trifluoride in a solvent such as dichloromethane at ambient temperature.

Preferred catalysts include the specific examples mentioned in WO 91/14694. Most preferably the chiral catalyst is (S,S)-[1,2-bis(3,5-di-tert-butylsalicylideneamino) cyclohexane]manganese (III) chloride as characterised on pages 33 and 34 of WO 91/14694.

It should be appreciated that the present invention specifically covers the preparation of all epoxide precursors to all specific examples in EP-A-0376 524 using the process hereinbefore described, especially the preparation of (3S,4S)-2,2-dimethyl-3,4-epoxy-6-pentafluoroethyl-2H-1-benzopyran.

Compounds of formula (C) are commercially available or may be prepared by reacting a compound of formula (G):

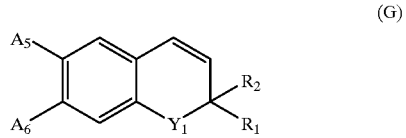

(G)

wherein $R_1$, $R_2$ and $Y_1$ are as defined in relation to formula (A) and wherein one of $A_5$ or $A_6$ represents a halogen atom, preferably bromine, and the other one of $A_5$ or $A_6$ represents a hydrogen atom, with a compound of formula (H):

$$CF_3CO.X \quad (H)$$

wherein X represents a leaving group; and thereafter where required, converting any moiety of formula $CF_3CO$— into a moiety $CF_3CH(OH)$— or $CF_3CF_2$—, or where appropriate preparing a protected form of such groups.

A suitable leaving group X is a trifluoroacetyloxy group.

The reaction between the compounds of formulae (G) and (H) may be carried out in any suitable aprotic solvent, such as tetrahydrofuran or dimethylformamide, at any temperature providing a convenient rate of formation of the required compound, such as at an elevated temperature, for example the reflux temperature of the solvent.

Preferably, the compound of formula (G) is in an activated form, for example in the form of a magnesium Grignard salt prepared in conventional manner.

Alternatively, a compound of formula (C) may be prepared by reacting a compound of the hereinbefore defined formula (G), with an alkali metal salt of pentafluoropropionic acid, suitably the sodium salt, and preferably in the presence of a copper (I) halide such as copper iodide.

The reaction between the compound of formula (G) and the pentafluoropropionic acid salt is suitably carried out in an aprotic solvent such as dimethylformamide, suitably at an elevated temperature such as the reflux temperature of the solvent.

Chiral catalysts mentioned in WO/91/14694 may be prepared according to the procedures in WO 91/14694 or by procedures analogous to them.

The present invention also provides a process for preparing compounds of formula (A) (hereinbefore described) or, where appropriate, a pharmaceutically acceptable salt thereof, or a pharmaceutically acceptable solvate thereof which comprises reacting a compound of formula (C) (hereinbefore described) in the presence of an oxygen source and a chiral catalyst as defined in WO/91/14694 and thereafter converting the resulting compound of formula (B) to a compound of formula (A) or, where appropriate, a pharmaceutically acceptable salt thereof, or a pharmaceutically acceptable solvate thereof.

It should also be appreciated that the present process specifically encompasses the preparation of all the specific examples in EP-A-0376 524 by reacting appropriate compounds of formula (C) in the presence of an oxygen source and a chiral catalyst a defined in WO/91/14694 and thereafter converting the resulting compound of formula (B) to a compound of formula (A).

A preferred compound of formula (A) is (3S,4R)-3,4-dihydro-2,2-dimethyl-4-(2-oxopiperidin-1-yl)-6-pentafluoroethyl-2H-1-benzopyran-3-ol, which is prepared by reacting (3S,4S)-2,2-dimethyl-3,4-epoxy-6-pentafluoroethyl-2H-1-benzopyran in the presence of an oxygen source and a chiral catalyst as defined in WO/91/14694 and thereafter converting the resulting epoxide compound to the compound of formula (A) as above.

Suitable methods for converting compounds of formula (B) to compounds of formula (A) involves reacting a compound of formula (B) with an activated form of a compound of formula (F):

$$R_{17}NHCOR_{16} \quad (F)$$

wherein $R_{16}$ and $R_{17}$ together represent a linking chain of formula —$A_3$—$A_4$—. In this process, a suitable activated form of a compound of formula (F) is an ionic form. Thus, in the reaction between a compound of formula (B) and a compound of formula (F), it is preferred that the reaction is carried out under basic conditions so as to facillitate the formation of the anion of the compound of formula (F), for example, in the presence of an alkali metal base such as potassium t-butoxide or sodium hydride. The reaction between the compounds of formula (B) and formula (F) may be carried out in any suitable aprotic solvent at a temperature that provides a convenient rate of formation of the compound of formula (A), such as at ambient temperature or at an elevated temperature, for example 40° C. Conveniently, the compound of formula (F) may itself be used as the solvent for the reaction between the compounds of formulae (B) and (F).

The following example illustrates the present invention.

EXAMPLE 1

Preparation of (3S,4S)-2,2-Dimethyl-3,4-epoxy-6-pentafluoroethyl-2H-1-benzopyran A titrated solution of sodium hypochlorite (2.5 L) water (4.2 L) and 0.05M sodium dihydrogen phosphate (16.0 g) in 2.7 L of deionised water was added to a 20 L flanged flask and the mixture adjusted to pH 11.3 with a few drops of orthophosphoric acid. This solution was added to a solution of 2,2-dimethyl-6-pentafluoroethyl-2H-1-benzopyran (0.751 kg) (which may be prepared according to the procedures outlined in EP-A-0376524) and (S,S)-[1,2-bis(3,5-di-tert-butylsalicylideneamino) cyclohexane]manganese (III)

chloride (17.1 g) (which may be prepared according to the procedures outlined in WO/91/14694 in dichloromethane (2.7 L) in a 25 L vessel and the mixture stirred at 42° C. overnight. The solution was cooled to 20° C., dichloromethane (4.1 L) was added, the mixture filtered through a bed of celite filter aid, washing the filter cake with dichloromethane (2.7 L) and the phases separated. The aqueous phase was washed with dichloromethane (6.7 L) and the combined organic phases were washed with brine (5.3 L) and evaporated to dryness to give 800 g of crude title product.

The crude epoxide was recrystallised from hot hexane (1.8 L) to give a first crop of a white solid which was filtered off and washed with 3×0.5 L portions of ice cold hexane. The solid was dried in vacuo at 50° C. for 3 hours.

The mother liquors were concentrated to 1.1 L and allowed to cool to 4° C. for 3–4 hours. The second crop of solid was filtered off and the product washed with 2×0.3 L of ice cold hexane. The solid was dried in vacuo at 50° for 3 hours.

Yield of first crop of title compound—533 g (67.2%).

Purity of first crop of title compound—98.7% (determined by quantitative HPLC).

Enantiomeric excess of first crop of title compound—99.7% (determined by quantitative chiral HPLC).

Yield of second crop of title compound—36.5 g (4.6%).

Purity of second crop of title compound—97.1% (determined by quantitative HPLC.

Enantiomeric excess of second crop of title compound—96.9% (determined by quantitative chiral HPLC).

We claim:

1. A process for preparing compounds of formula (B)

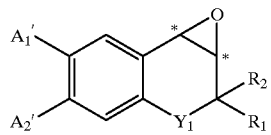

(B)

wherein:
one of $A_1'$ or $A_2'$ represents hydrogen and the other represents a group $CF_3$—Y— wherein Y represents —$CF_2$—, >C=O, or —CH(OH)—, or $A_1'$ and $A_2'$ are groups convertible to $A_1$ and $A_2$ respectively;
$Y_1$ represents —O—, —$CH_2$— or $NR^O$ wherein $R^O$ is hydrogen, alkyl or alkylcarbonyl; $R_1$ and $R_2$ independently represent hydrogen or alkyl; or $R_1$ and $R_2$ together represent a $C_{2-7}$ polymethylene moiety;
$R_3$ represents hydrogen, hydroxy, alkoxy or acyloxy and $R_4$ is hydrogen or $R_3$ and $R_4$ together represent a bond;
which process comprises reacting a compound of formula (C):

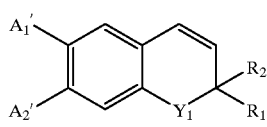

(C)

wherein the variables $A_1'$, $A_2'$, $Y_1$, $R_1$ and $R_2$ are as defined above, in the presence of an oxygen source and a chiral catalyst, wherein the chiral catalyst is selected from the group consisting of compounds with the structure of formula (D):

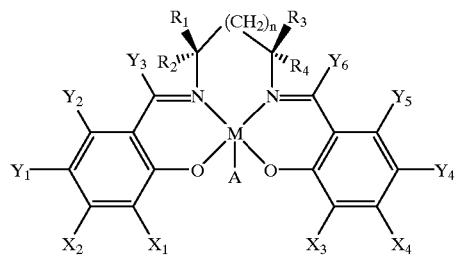

(D)

wherein M is a transition metal ion, A is an anion, and n is either 0, 1, or 2; at least one of X1 or X2 is selected from the group consisting of silyl, aryl secondary alkyl and tertiary alkyl; and at least one of X3 or X4 is selected from the same group; Y1, Y2, Y3, Y4, Y5, and Y6 are independently selected from the group consisting of hydrogen, halide, alkyl, aryl group, silyl group, and alkyl group bearing hetero-atoms selected from the group consisting of alkoxy and halide; and at least one of R1, R2, R3 and R4 is selected from a first group consisting of H, $CH_3$, $C_2H_5$, and primary alkyl; wherein if R1 is selected from said first group, then R2 and R3 are selected from a second group consisting of aryl groups, heteroatom-bearing aromatic groups, secondary alkyls and tertiary alkyls; if R2 is selected from said first group, then R1 and R4 are selected from said second groups if R3 is selected from said first group, then R1 and R4 are selected from said second group; if R4 is selected from said first group, then R2 and R3 are selected from said second group; or compounds with the structure of formula (I):

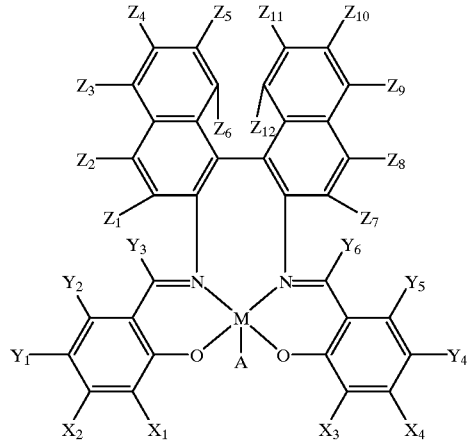

(I)

wherein M is a transition metal ion and A is an anion; where at least one of X1 or X2 is selected from the group consisting of aryl, primary alkyl, secondary alkyl, tertiary alkyl, and hetero atoms; where at least one of X3 or X4 is selected from the group consisting of aryl, primary alkyl, secondary alkyl, tertiary all, and hetero atoms; and where Y1, Y2, Y3, Y4, Y5, Y6, Z1, Z2, Z3, Z4, Z5, Z6, Z7, Z8, Z9, Z10, Z11, and Z12 are independently selected from the group consisting of hydrogen, halide, alkyl, aryl, and alkyl group bearing hetero atoms; or compounds with the structure of formula (J):

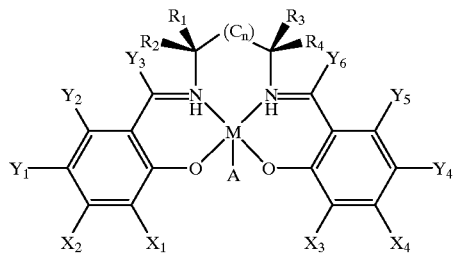

(J)

where M is a transition metal ion and A is an anion; where n is either 0, 1, or 2; where at least one of X1 or X2 is selected from the group consisting of aryl, primary alkyl, secondary alkyls tertiary alkyl, and hetero atoms, where at least one of X3 or X4 is selected from the group consisting of aryl, primary alkyl, secondary alkyl, tertiary alkyl, and hetero atoms; where at least one of Y1 or Y2 is selected from the group consisting of aryl, primary alkyl, secondary alkyl, tertiary alkyl, and hetero atoms; where at least one of Y4 or Y5 is selected from the group consisting of aryl, primary alkyl, secondary alkyl, tertiary alkyl, and hetero atoms: where Y3 and Y6 are independently selected from the group consisting of hydrogen and primary alkyl groups; where either one or two of R1, R2, R3 and R4 is hydrogen; where, if R 1 is hydrogen, then R3 is a primary alkyl; where, if R2 is hydrogen, then R4 is a primary alkyl; where, if R3 is hydrogen, then R1 is a primary alkyl; and where, if R4 is hydrogen, then R2 is a primary alkyl; or compounds with the structure of formula (K):

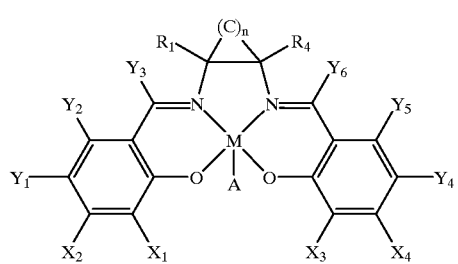

(K)

where M is a transition metal ion and A is an anion; where n is either 3, 4, 5 or 6; where at least one of X1 or X2 is selected from the group consisting of aryl, primary alkyl, secondary alkyls tertiary alkyl, and hetero atoms, where at least one of X3 or X4 is selected from the group consisting of aryl, primary alkyl, secondary alkyl, tertiary alkyl, and hetero atoms; where at least one of Y1 or Y2 is selected from the group consisting of aryl, primary alkyl, secondary alkyl, tertiary alkyls, and hetero atoms, where at least one of Y4 or Y5 is selected from the group consisting of aryl, primary alkyl secondary alkyl, tertiary alkyl, and hetero atoms: where Y3, and Y6 are independently selected from the group consisting of hydrogen and primary alkyl groups; where R1 and R4 are trans to each other and at least one of R1 and R4 is selected from the group consisting of primary alkyl and hydrogen; and where the carbons in the $(C)_n$ portion have substituents selected from the group consisting of hydrogen, alkyl, aryl, and heteroatoms.

2. A process according to claim 1 wherein in the compound of formula (B) $A_1'$ is $CF_3CF_2$, $A_2'$ is hydrogen, $Y_1$ is oxygen and $R_1$ and $R_2$ are both methyl.

3. A process according to claim 1 wherein the compound of formula (B) is 3S,4S-2,2-dimethyl-3,4-epoxy-6-pentafluoroethyl-2H-1-benzopyran.

4. A process according to claim 1 wherein the chiral catalyst is of formula (D).

5. A process according to claim 4 wherein the chiral catalyst is of formula (E):

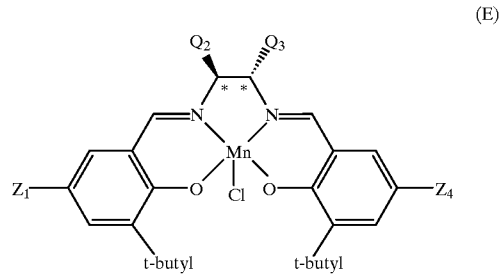

(E)

wherein $Z_1$ and $Z_4$ are the same and are selected from the group consisting of methyl, t-butyl or methoxy and $Q_2$ and $Q_3$ are either both phenyl or together with the carbon atoms to which they are attached form an hexyl ring.

6. A process according to claim 5 wherein the $Z_1$ and $Z_4$ are both t-butyl and $Q_2$ and $Q_3$ together with the carbon atom to which they are attached form a hexyl group.

7. A process according to claim 6 wherein the chiral catalyst is (S,S)-[1,2-bis(3,5-di-tert-butylsalicylideneamino) cyclohexane]manganese (III) chloride.

8. A process according to claim 1 further comprising the step of converting the compound of formula (B) into a compound of formula (A):

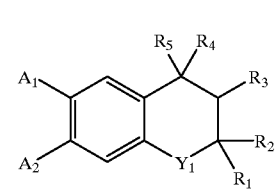

(A)

or, where appropriate, a pharmaceutically acceptable salt thereof, or a pharmaceutically acceptable solvate thereof wherein:

one of $A_1$ or $A_2$ represents hydrogen and the other represents a group $CF_3$—Y— wherein Y represents —$CF_2$—, >C=O, or —CH(OH)—;

$Y_1$ represents —O—, —$CH_2$— or $NR^O$ wherein $R^O$ is hydrogen, alkyl or alkylcarbonyl; $R_1$ and $R_2$ independently represent hydrogen or alkyl; or $R_1$ and $R_2$ together represent a $C_{2-7}$ polymethylene moiety;

$R_3$ represents hydrogen, hydroxy, alkoxy or acyloxy and $R_4$ is hydrogen or $R_3$ and $R_4$ together represent a bond;

$R_5$ represents either a moiety of formula (a):

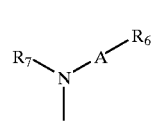

(a)

wherein A represents >C=X wherein X is O, S or $NR_8$ wherein $R_8$ represents CN, $NO_2$, $COR_9$ wherein $R_9$ is alkyl, amino, monoalkylamino, fluoroalkyl, phenyl or substituted phenyl or $R_8$ is $SO_2R_9$ wherein $R_9$ is as defined above, or A represents a bond;

when A represents >C=X wherein X is O or S, then $R_6$ is hydrogen; alkyl optionally substituted by one or more groups or atoms selected from halogen, hydroxy, alkoxy, alkoxycarbonyl, carboxy or an ester or amide thereof, amino, monoalkylamino or dialkylamino; alkenyl; amino optionally substituted by an alkyl or alkenyl group or by an alkanoyl group optionally substituted by up to three halo atoms, by a phenyl group optionally substituted by alkyl, alkoxy or halogen; substituted or unsubstituted aryl or substituted or unsubstituted heteroaryl; and $R_7$ represents hydrogen or alkyl;

or $R_6$ and $R_7$ together represent a linking chain of formula —$A_3$—$A_4$—, $A_3$ being attached to the nitrogen atom of the moiety —N—A— and $A_4$ being attached to the group A on the said moiety, and wherein $A_3$ represents a substituted or unsubstituted methylene group, $A_4$ represents 2 or 3 linking members, one of the linking members optionally representing O, S or NR and the other linking members each independently representing a substituted or unsubstituted methylene group;

R represents hydrogen, alkyl, alkanoyl, phenyl $C_{1-4}$-alkyl, arylcarbonyl wherein the aryl group may be substituted or unsubstituted; or R is mono- or bi-cyclic- heteroarylcarbonyl;

when A represents >C=X wherein X represents $NR_8$, then $R_6$ represents —$NH.R_{10}$ wherein $R_{10}$ is hydrogen, alkyl, $C_{3-6}$ cycloalkyl, alkenyl or alkynyl and $R_7$ is hydrogen or alkyl; or $R_7$ and $R_{10}$ together represent $C_{2-4}$ polymethylene;

when A represents a bond, then $R_6$ and $R_7$ together with the nitrogen atom to which they are attached, form an unsaturated heterocyclic ring having 5 to 7 ring atoms, which ring atoms comprise up to 2 further nitrogen atoms and a carbon atom, the carbon atom being substituted with either an oxo group or a thioxo group, the remaining ring atoms being substituted or unsubstituted;

or $R_5$ represents a moiety of formula (b):

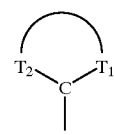

(b)

wherein $T_1$ represents >C—OH or $N(O)_n$ wherein n is zero or 1 and $T_2$ together with C—$T_1$, when $T_1$ is >C—OH, represents an optionally substituted aryl group or $T_2$ together with $CT_1$, when $T_1$ is $N(O)_n$, represents an optionally substituted, N-heteroaryl group;

or $R_5$ represents a moiety of formula (c):

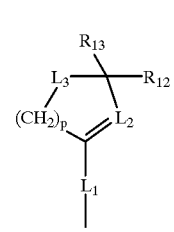

(c)

wherein $L_1$ represents O or $NR_{11}$ wherein $R_{11}$ represents hydrogen, alkyl, formyl, acetyl or hydroxymethyl, $L_2$ represents N or $CL_4$ wherein $L_4$ is hydrogen, halogen, formyl or hydroxymethyl, $L_3$ represents $CH_2$, O, S, >$CHL_5$ wherein $L_5$ is halogen or $NL_6$ wherein $L_6$ is hydrogen or alkyl and $R_{12}$ and $R_{13}$ each independently represent hydrogen or alkyl or $R_{12}$ together with $R_{13}$ represents oxo or thioxo; and p represents 1, 2 or 3; which process comprises reacting a compound of formula (B) as defined in claim 1 with an activated form of a compound of formula (F):

$R_{17}NHCOR_{16}$ (F)

wherein $R_{16}$ and $R_{17}$ together represent a linking chain of formula —$A_3$—$A_4$—, optionally comprising the further step of forming a pharmaceutically acceptable salt or a pharmaceutically acceptable solvate of the compound of formula (A).

9. A process according to claim 8 in which the compound of formula (A) is (3S,4R)-3,4-dihydro-2,2-dimethyl-4-(2-oxopiperidin-1-yl)-6-pentafluoroethyl-2H-1-benzopyran-3-ol.

* * * * *